US00PP19963P2

(12) United States Plant Patent
Rendle

(10) Patent No.: US PP19,963 P2
(45) Date of Patent: Apr. 28, 2009

(54) ***CORDYLINE* PLANT NAMED 'PARADISE'**

(50) Latin Name: *Cordyline australis*
Varietal Denomination: Paradise

(76) Inventor: Arthur Rendle, P.O. Box 113033, New Market, Auckland (NZ)

( * ) Notice: Subject to any disclaimer, the term of this patent is extended or adjusted under 35 U.S.C. 154(b) by 0 days.

(21) Appl. No.: 11/978,399

(22) Filed: Oct. 29, 2007

(51) Int. Cl.
*A01H 5/00* (2006.01)

(52) U.S. Cl. ..... Plt./383
(58) Field of Classification Search ..... Plt./383
See application file for complete search history.

*Primary Examiner*—Kent L Bell

(57) ABSTRACT

A new and distinct *Cordyline* cultivar named 'Paradise' is disclosed, characterized by very stable, strongly variegated foliage of pink/green/yellow and excellent performance in drought and high heat.

1 Drawing Sheet

Figure 1:
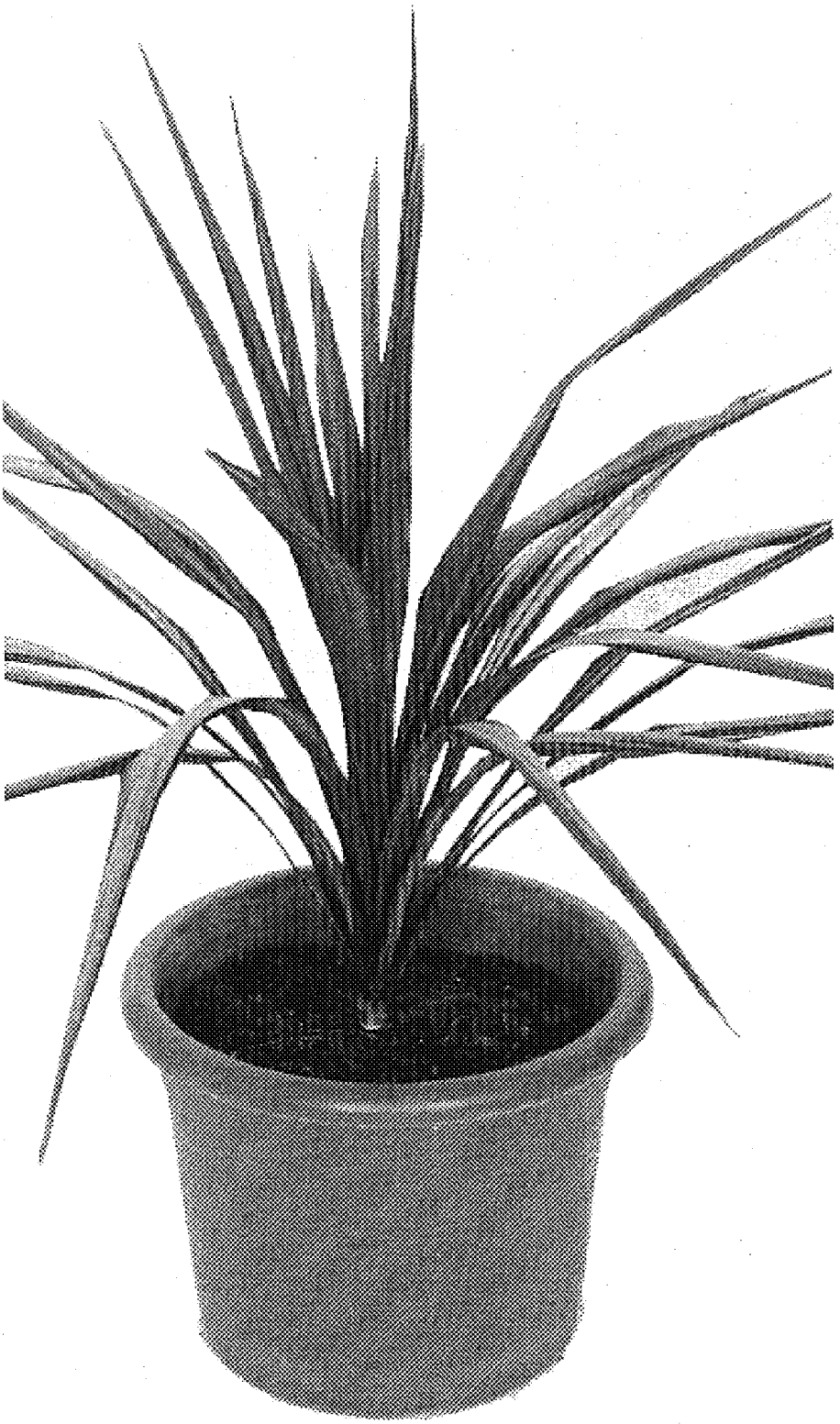

Latin name of the genus and species: *Cordyline australis*.
Variety denomination: 'PARADISE'.

BACKGROUND OF THE INVENTION

The new cultivar is a product of a planned breeding program. The new variety originated from a cross pollination of the seed parent *Cordyline australis* 'Purple Tower,' an unpatented cultivar and the pollen parent *Cordyline australis* 'Torbay Dazzler,' also unpatented, made by the inventor during December 1995.

It was discovered by the inventor, Arthur George Rendle, a citizen of New Zealand, in Spring of 1996 New Plymouth, New Zealand.

Asexual reproduction of the new cultivar 'Paradise' was first performed in Auckland, New Zealand, in a commercial greenhouse by vegetative root cuttings. Subsequently 'Paradise' has been reproduced by micro-propagation and has shown that the unique features of this cultivar are stable and reproduced true to type through 12 generations.

SUMMARY OF THE INVENTION

The cultivar 'Paradise' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Paradise' These characteristics in combination distinguish 'Paradise' as a new and distinct *Cordyline* cultivar:

1. Strongly variegated foliage.
2. Unique background foliage color near RHS 199A.
3. Unique mid-foliage color near RHS 35C.
4. Stable and consistent foliage variegation.

Plants of the new cultivar 'Paradise' are similar to plants of the seed parent; *Cordyline australis* 'Purple Tower', in most horticultural characteristics, however, plants of the new cultivar 'Paradise' have a strong colorful foliage variegation while the seed parent 'Purple Tower' has solid foliage in a flat maroon color. Additionally, the new variety has wider leaves.

Plants of the new cultivar 'Paradise' are similar to plants of the pollen parent; *Cordyline australis* 'Torbay Dazzler', in most horticultural characteristics, however, plants of the new cultivar 'Paradise' have foliage variegation that is mostly dark pink with green margins and slight yellow striations, while the pollen parent 'Torbay Dazzler' has green and yellow foliage variegation. Additionally, the leaf base of the new variety is the same color as the rest of the leaf while the pollen parent has a solid red leaf base.

The most similar commercial *Cordyline australis* varieties available to compare to 'Paradise' are the parent varieties.

BRIEF DESCRIPTION OF THE PHOTOGRAPH

The accompanying photograph in FIG. 1 illustrates in full color a typical plant of 'Paradise' grown in a greenhouse. This plant is approximately 8 months old, shown in a 5 liter pot. The photograph was taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart except where general terms of ordinary dictionary significance are used. The following observations and measurements describe 'Paradise' plants grown in a greenhouse in Las Pallas, Murcia, Spain during the Winter of 2006 through Spring of 2007. Temperatures ranged from 5° C. to 12° C. at night to 5° C. to 20° C. during the day. Measurements and numerical values represent averages of typical plant types.

Botanical classification: *Cordyline australis* cultivar 'Paradise.'

PROPAGATION

Time to rooting: 10 to 14 days at approximately 15° C. soil temperature, 22° C. air temperature.
Root description: Fine, fibrous.

PLANT

Growth habit: Upright perennial.
Height: Approximately 100 cm in a 5 liter pot. Approximately 500 cm after one year planted in the ground in a garden.
Blooming period: Not observed in commercial applications.
Plant Spread: Approximately 40 cm in a 5 liter pot. Approximately 100 cm after one year planted in the ground in a garden.
Growth Rate: Moderate to vigorous.
Branching Characteristics: Upright, non-branching.
Diameter of stem: Approximately 2.5 cm.
Stem length, measured as leafless section: Approximately 5 cm on a 1 year old plant. As the plant ages, lower leaves fall off, exposing a longer section of stem.
Stem color: Near RHS Greyed-Orange N170D.
Number of leaves per stem: Approximately 300.
Age of plant described: Approximately 8 months.

FOLIAGE

Leaf:
*Arrangement.*—Whorled.
*Average length.*—Approximately 75 cm.
*Average width.*—Approximately 3 cm.
*Shape of blade.*—Linear.
*Apex.*—Sharply acute.
*Margin.*—Entire.
*Texture of top surface.*—Smooth, glossy.
*Texture of bottom surface.*—Smooth, leathery.
*Leaf internode length.*—2 mm.
*Color.*—Young foliage upper side: Near R.H.S. 35C and 199A. Young foliage underside: Near R.H.S. 35C and 199A. Mature foliage upper side: Near R.H.S. 35C and 199A. Mature foliage under side: Near R.H.S. 35C and 199A.
*Venation.*—Type: Linear Venation coloration: Not visible due to variegation in foliage.
Petiole: Not present

FLOWER

Flowering has not been observed, and is not commercially important in this cultivar.

OTHER CHARACTERISTICS

Disease resistance: Neither resistance nor susceptibility to diseases or pests has been observed in this variety.
Drought tolerance and cold tolerance: Hardy to −5° C. Tolerates temperatures above 40° C. Excellent drought tolerance. In a garden setting, 'Paradise' can tolerate a minimum of 3 to 4 weeks without water undamaged.
Fruit/Seed production: Not observed.

What is claimed is:

1. A new and distinct cultivar of *Cordyline* plant named 'Paradise' as herein illustrated and described.

* * * * *